United States Patent
Leet et al.

(10) Patent No.: US 6,218,398 B1
(45) Date of Patent: Apr. 17, 2001

(54) NOCATHIACIN ANTIBIOTICS

(75) Inventors: John E. Leet; Helen A. Ax, both of Madison; Donald R. Gustavson, Torrington; Daniel M. Brown, Killingworth; Laura Turner, Mystic; Kimberly Brown, Rockfall; Wenying Li, Middletown; Kin S. Lam, North Haven, all of CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/351,791

(22) Filed: Jul. 13, 1999

Related U.S. Application Data

(60) Provisional application No. 60/108,716, filed on Nov. 17, 1998, and provisional application No. 60/093,021, filed on Jul. 16, 1998.

(51) Int. Cl.[7] .......................... C07D 515/22; A61K 31/44
(52) U.S. Cl. ............................. 514/279; 540/450
(58) Field of Search ............................. 540/456; 514/279

(56) References Cited

PUBLICATIONS

Cohen, "Antimicrobial resistance: prognosis for public health," *Trends in Microbiology*, vol. 2, No. 10, Oct. 1994, pp. 422–425.

Sasaki, et al., "MJ347–81F4 A & B, Novel Antibiotics from *Amycolatopsis* sp.: Taxonomic Characteristics, Fermentation, and Antimicrobial Activity," *Journal of Antibiotics*, vol. 51, No. 8, 1998, pp. 715–721.

Pascard, et al., "Highly Modified Cysteine–Containing Antibiotics. Chemical Structure and Configuration of Nosiheptide," *J. Am. Chem. Soc.*, 99, 1977, pp. 6418–6423.

Benazet, et al., "Nosiheptide, a sulfur–containing peptide antibiotic isolated from *Streptomyces actuosus* 40037," *Experientia*, 36, 1980, pp. 414–416.

Mocek, et al., "Biosynthesis of the Modified Peptide Antibiotic Nosiheptide in *Strptomyces actuosus*," *Journal of the American Chemical Society*, vol. 115, No. 17, Aug. 25, 1993, pp. 7557–7568.

Steinberg, et al., "Glycothiohexides, Novel Antibiotics Produced by"*Sebekia*"sp. LL–14E605. I. Taxonomy, Fermentation and Biological Evaluation," *Journal of Antibiotics*, vol. 47, No. 8, Aug. 1994, pp. 887–893.

Northcote, et al., "Glycothiohexide α, A Novel Antibiotic Produced by"*Sebekia*"sp. LL–14E605. II. Isolation and Physical–chemical Characterization," *Journal of Antibiotics*, vol. 47, No. 8, Aug. 1994, pp. 894–900.

Northcote, et al., "Glycothiohexide α, A Novel Antibiotic Produced by"*Sebekia*"sp. LL–14E605. III. Structural Elucidation," *Journal of Antibiotics*, vol. 47, No. 8, Aug. 1994, pp. 901–908.

*Primary Examiner*—Bruck Kifle
(74) *Attorney, Agent, or Firm*—Samuel J. DuBoff

(57) ABSTRACT

Novel thiazolyl peptide antibiotic compounds, including nocathiacin I, II and III, are disclosed. Also, novel microorganism ATCC-202099 is disclosed.

7 Claims, 12 Drawing Sheets

NOCATHIACIN ANTIBIOTICS

This application claims the benefit of U.S. Provisional Application Nos. 60/108,716 filed Nov. 17, 1998 and 60/093,021 filed Jul. 16, 1998.

BACKGROUND

The emergence of bacterial resistance to a number of antimicrobial agents such as beta-lactam antibiotics, macrolides, quinolones, and vancomycin is becoming a major worldwide health problem. (Cohen, M. L. Antimicrobial resistance: prognosis for public health. *Trends Microbiol.* 1994, 2, 422–425). The most significant problem in clinical practice is the increase in incidence of methicillin-resistant *Staphylococcus aureus* (MRSA) strains. At present, the only effective treatment for multiple resistant MRSA infections is vancomycin. However, there are recent reports of emerging vancomycin resistance in some MRSA isolates. Another group of clinically relevant multiple drug resistant bacteria that have emerged recently are the Enterococci. The emerging resistance of the important community acquired pathogen *Streptococcus pneumoniae* to penicillin and other antibacterials is also becoming a worldwide health problem. Multi drug-resistant strains of *Mycobacterium tuberculosis* have surfaced in several countries including the United States. The emergence and spread of resistant nosocomial and community-acquired pathogens is generating a great threat to public health worldwide. There is an urgent need to discover new agents to treat patients infected with multidrug-resistant bacteria. The present invention addresses this need.

New thiazolyl peptide antibiotics, (designated herein as nocathiacin I, II and III, or collectively as nocathiacin) having inhibitory activity at the nanomolar level against Gram-positive bacteria (e.g. multiple drug resistant *Enterococcus faecium*), are described. The novel antibiotics described herein were isolated from cultured broth of Nocardia sp. ATCC-202099. Known members of the thiazolyl peptide class of antibiotics such as thiostrepton and nosiheptide, and glycothiohexide-α have been reported to exhibit potent antimicrobial activity against Gram-positive bacteria in vitro, with no reported activity in vivo. The novel antibiotics disclosed herein exhibit in vivo efficacy in a systemic *Staph. aureus* infection model in mice.

Nocathiacin I has been previously described by J. E. Leet et al (U.S. Provisional Patent Application Serial No. 60/093,021 filed Jul. 16, 1998) commonly owned by Applicant herein, and Sasaki, T. et al, *J. of Antibiotics* 51, No. 8, pp. 715–721 (published Aug. 25, 1998). The novel nocathiacin antibiotics of this invention are related to but clearly distinguishable from nosiheptide (Prange T. et al., *J. Am Chem Soc.* 99, 6418 (1977); Benazet, F. et. al. *Experientia* 36, 414 (1980); Floss, H. G. et al., *J. Am Chem Soc.* 115, 7557 (1993); glycothiohexides (Steinberg, D. A. et al, *J. Antibiot.* 47, 887 (1994); M. D. Lee et al, *J. Antibiot.* 47, 894 (1994); M. D. Lee et al, *J. Antibiot.* 47, 901 (1994); U.S. Pat. No. 5,451,581, 1995), and Antibiotic S-54832A (U.S. Pat. No. 4,478,831, 1984).

SUMMARY OF THE INVENTION

The invention concerns novel thiazolyl peptide antibiotic compounds nocathiacin I, II and III. The antibiotics of this invention can be isolated and purified from Nocardia sp. (strain WW-12651, ATCC-202099) fermentation broths.

The invention also deals with pharmaceutical compositions and methods for treating bacterial infections with nocathiacin I, II and III antibiotics, as well as a biologically pure culture of Nocardia sp. strains from which the antibiotics are obtained. The invention includes all pharmaceutically acceptable derivatives of nocathiacin antibiotics, such as pharmaceutically acceptable salts and esters thereof.

The utility of the subject compound in the treatment of bacterial infections is based upon the expectation that compounds which inhibit Gram-positive bacteria in vitro and in vivo can be used as antibiotics in mammals, and in particular, humans. The compounds of this invention were found to have antibiotic activity, particularly in inhibiting the growth of Gram-positive bacteria.

DETAILED DESCRIPTION OF THE INVENTION

Figure 1:
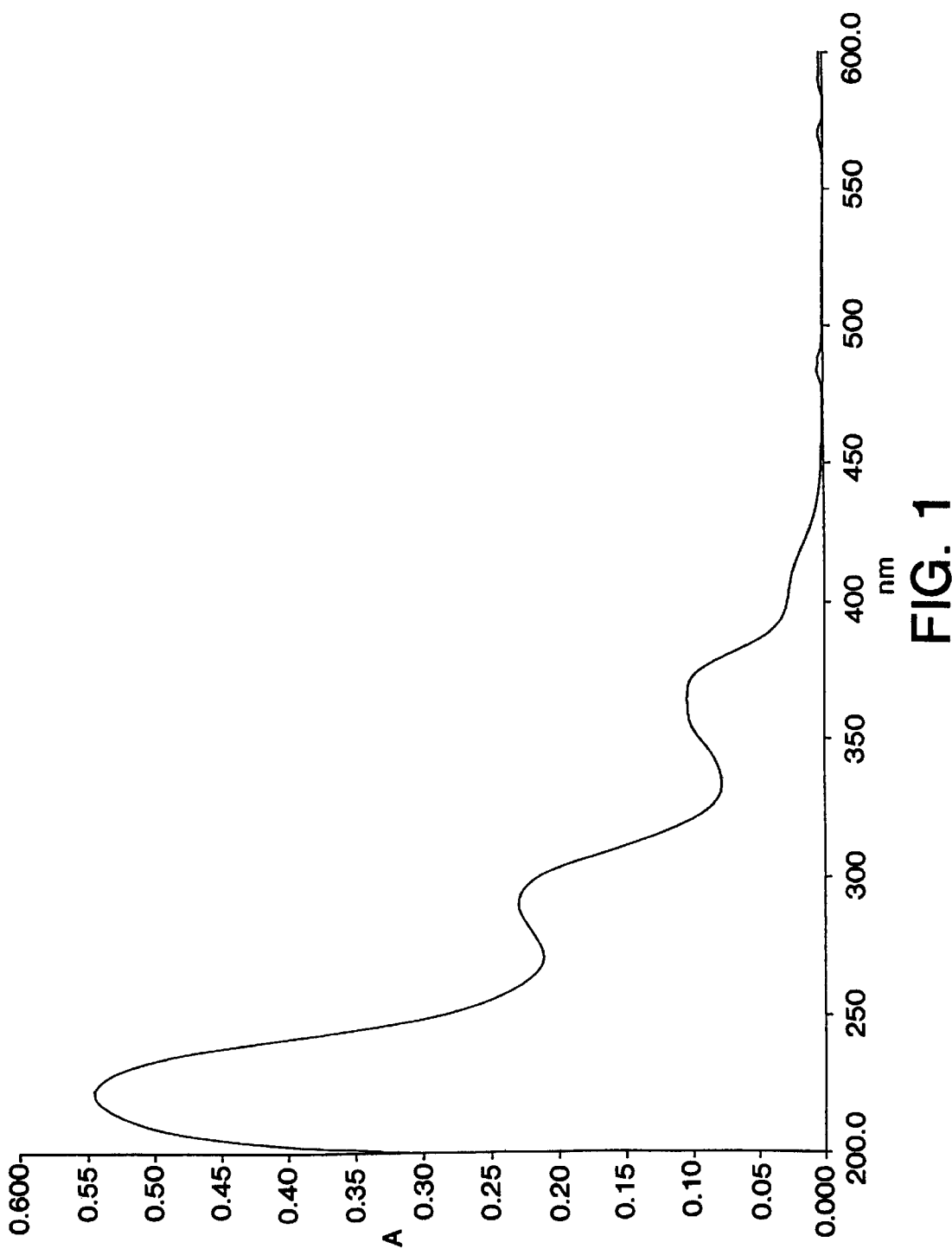
FIG. 1 shows the ultraviolet absorption (UV) spectrum of nocathiacin I.

The antibiotic compounds called nocathiacin I, II and III were discovered in a program designed to find novel compounds produced by fermentation. The subject nocathiacin compounds were isolated from a cultured fermentation broth of Nocardia sp. strain WW-12651 (ATCC-202099), and were purified by extraction and chromatographic procedures to yield solids of amorphous character.

Description of the Microorganism

The microorganism which may be used for the production of nocathiacin antibiotics is a strain of Nocardia sp. isolated from a soil sample collected in New Mexico. The culture (strain WW-12651) was deposited on Mar. 4, 1998 with the American Type Culture Collection (ATCC) in Rockville, Md., with the accession number of ATCC-202099. The ATCC deposit meets all of the requirements of the Budapest treaty. The dormant culture is also maintained at the Bristol-Myers Squibb Pharmaceutical Research Institute Culture Collection at 5 Research Parkway, Wallingford, Conn. 06492. In addition to the specific microorganism described herein, it should be understood that mutants, such as those produced by the use of chemical or physical mutagens including X-rays, etc. and organisms whose genetic makeup has been modified by molecular biology techniques, may also be cultivated to produce nocathiacin antibiotics.

Microscopic studies on strain WW-12651 were carried out on ISP morphology media (ISP2, ISP3, ISP4, ISP5, and ISP7) and observations were made at 7, 14, and 21 days of incubation at 28° C. according to the International Streptomyces Project manual recommendations.

Growth on ISP4 medium develops as yellow cream colored colonies. The aerial mycelium is white and fragments extensively. Under light microscopy, spore chains are observed in the vegetative mycelium while few to no spore chains are seen in the cob web-like mycelium. The observed morphology classifies this organism as a non-Streptomyces type. A light brown-orange reverse color is observed on salts-starch agar (ISP4). There were no diffusable pigments produced on any of the ISP media. Melanoid pigments are not formed on tyrosine agar (ISP7) and are not detected by the modified Arai and Mikami melanin formation test.

The amino acid components of the cell wall are alanine, L-glutamic acid, aspartic acid, and the meso-diaminopimelic acid isomer. The sugar components of the cell wall are galactose, arabinose, and ribose. Carbon utilization studies showed that glucose, mannitol, sucrose, xylose and fructose (weak) were utilized for growth when incorporated into inorganic salts agar (ISP9) as sole carbon sources. Arabinose, inositol, raffinose, and rhamnose were not utilized for growth as sole carbon sources with ISP9. Based on the above characteristics and analysis of mycolic acids, this organism has been characterized as a member of the genus Nocardia.

Fermentation of Nocardia sp. (strain WW-12651)

The production of nocathiacin antibiotics may be carried out by cultivating Nocardia sp. (strain WW-12651) in a suitable nutrient medium under conditions described herein, preferably under submerged aerobic conditions, until a substantial amount of nocathiacins are detected in the fermentation, harvesting by extracting the active components from the mycelial growth with a suitable solvent, concentrating the solution containing the desired components, then subjecting the concentrated material to chromatographic separation to isolate the compounds from other metabolites also present in the cultivation medium.

Production of nocathiacin can be effected at temperature conducive to satisfactory growth of the producing organism, e.g. 16° C. and 40° C., but it is preferable to conduct the fermentation at 22° C. to 32° C. The aqueous medium is incubated for a period of time necessary to complete the production of nocathiacin as monitored by high pressure liquid chromatography (HPLC) usually for a period of about 1–6 days, on a rotary shaker operating at about 50 rpm to 300 rpm, preferably at 150 rpm to 250 rpm.

Growth of the microorganisms may be achieved by one of ordinary skill of the art by the use of appropriate medium. Broadly, the sources of carbon include glucose, fructose, mannose, maltose, galactose, mannitol and glycerol, other sugars and sugar alcohols, starches and other carbohydrates, or carbohydrate derivatives such as dextran, cerelose, as well as complex nutrients such as oat flour, corn meal, millet, corn and the like. The exact quantity of the carbon source which is utilized in the medium will depend in part, upon the other ingredients in the medium, but it is usually found that an amount of carbohydrate between 0.5 to 10 percent by weight of the medium is satisfactory. These carbon sources can be used individually or several such carbon sources may be combined in the same medium. Certain carbon sources are preferred as hereinafter set forth.

The sources of nitrogen include amino acids such as glycine, arginine, threonine, methionine and the like, ammonium salt, as well as complex sources such as yeast extracts, corn steep liquors, distiller solubles, soybean meal, cotttonseed meal, fish meal, and the like. The various sources of nitrogen can be used alone or in combination in amounts ranging from 0.05 to 5 percent by weight of the medium.

Among the nutrient inorganic salts, which can be incorporated in the culture media, are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

Typically, Nocardia sp. (strain WW-12651) was grown in a 500 ml flask containing 100 ml of vegetative medium consisting of the following per liter of deionized water: starch, 20 g; dextrose, 5 g; N-Z case, 3 g; yeast extract, 2 g; fish meat extract, 5 g; calcium carbonate, 3 g. The culture was allowed to incubate for 3 days at 32° C. on a rotary shaker operating at 250 rpm. The vegetative culture was mixed with equal volume of cryoprotective solution consisting of 100 g sucrose and 200 g glycerol per liter of deionized water. Four ml portions of this mixture were transferred to sterile cryogenic tube (5 ml capacity) and were frozen in a dry ice-acetone bath. The frozen vegetative cultures so obtained were then stored at −80° C.

Seed culture for the production of nocathiacin antibiotics was prepared by transferring 4 ml of the cryopreservative culture to a 500 ml flask containing 100 ml of sterile vegetative medium having the same composition as the above. The seed culture was incubated at 28° C. to 32° C. for 3 days on a rotary shaker operating at 250 rpm. Four ml of this seed culture was inoculated into 500 ml flask containing 100 ml of production medium consisting of the following per liter of deionized water: HY Yest 412, 10 g; glucose, 20 g; Nutrisoy, 10 g. This is the preferred production medium. The production culture was incubated at 24° C. to 32° C. on a rotary shaker operating at 180 rpm to 250 rpm. Optimal production of nocathiacin antibiotics was generally obtained at 4–5 days of fermentation.

When the nocathiacin I, II or III compounds are employed as pharmaceutical compositions for the treatment of bacterial infections, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in sustained release form. For most large mammals the total daily dosage is from about 1 to 100 mg, preferably from about 2 to 80 mg. dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The term pharmaceutically acceptable salt includes solvates, hydrates, acid addition salts and quaternary salts. The acid addition salts are formed from a nocathiacin I, II or III compound having a basic nitrogen and a pharmaceutically acceptable inorganic or organic acid including but not limited to hydrochloric, hydrobromic, sulfuric, phosphoric, methanesulfonic, acetic, citric, malonic, succinic, fumeric, maleic, sulfamic, or tartaric acids. Quaternary salts are formed from a basic nocathiacin I, II or III compound and an alkyl or arylalkyl halide, preferably methyl or benzyl bromide.

It is understood that the nocathiacin compounds of the invention herein include the various stereoisomers that may exist.

Description of the MREF Assay Procedures

The biological activity of the nocathiacin antibiotic compounds was discovered when a crude extract prepared from the producing Nocardia sp. (ATCC 202099) culture was tested in a high throughput screening assay. The screen is based on growth inhibition of *Enterococcus faecium* strain A28152 inoculated into agar growth media. This *E. faecium* strain is resistant to many antibiotics, including penicillin G, vancomycin, ciprofloxacin, teicoplanin, tetracycline, streptomycin, gentamicin, erythromycin, clindamycin and rifampin. It is sensitive to chloramphenicol and, to a lesser extent, imipenem. Hence the name MREF, which stands for Multi-drug Resistant *E. faecium*.

*E. faecium* strain A28152 is inoculated into Brain Heart Infusion Broth nutrient medium and cultured to log phase growth by incubation at 37° C. with agitation. Periodically, 0.2 mL aliquots of culture are withdrawn and pipetted into a well in a 96 well clear plastic flat-bottom plate. The optical density at 595 nm is then measured. When the optical density is in the range of 0.2 to 0.4, the bacteria are harvested by centrifugation at 1000×g for 10 minutes. The cell pellet is resuspended in Mueller-Hinton II growth media. This suspension of cells is then inoculated into molten Mueller-Hinton II growth media containing 1% Difco agar at a temperature of 48° C., to give an inoculated cell density of $1 \times 10^7$ cells/mL. 25 mL of the cell suspension is poured into a sterile rectangular plate. A special sterile plastic lid that mates with the plate is placed on top of the plate while the media is still molten. This lid contains plastic pegs arranged in the standard 8×12 format. The media is allowed to gel at room temperature for 15 minutes, then the pin lid is removed. Small concave impressions remain in the gelled media where the pins contacted the surface of the molten media. These serve as sample loading zones.

Samples to be tested in the screen are dissolved to a concentration of 300 $\mu$M in 100% dimethylsulfoxide (DMSO). A 6 $\mu$L volume of each sample is applied to individual sample loading zones on the plate. After sample loading, the plate is incubated at 37° C. for 24 hours. Growth inhibition is detected as a clear circular zone surrounding the sample zone. Outside of this zone, where the bacterial growth is unimpeded, the agar medium is turbid due to bacterial growth. DMSO alone does not cause any detectable growth inhibition under these conditions. Samples of chloramphenicol and DMSO are included on each plate as positive and negative controls, respectively.

For Thin Layer Chromatography (TLC) biograms for use in identifying the active principal(s) present in the producing Nocardia sp. (ATCC 202099) culture, the materials used included Bio-Assay Dishes from Nunc Nalge International used for agar diffusion assays. The dish measures 243×243× 18 mm and provides a 530 $cm^2$ microbiological culture area. The TLC plate is attached to the bio-assay dish and then an agar overlay is poured slowly covering the entire TLC plate and the bottom of the bio-assay dish. The agar overlay consists of 200 mL Mueller-Hinton II agar medium supplemented with 0.5% defibrinated sheep's blood and $1 \times 10^6$ cells/mL of strain A28152, the drug-resistant *Enterococcus faecium* strain. Once cool, the TLC biogram is incubated at room temperature for approximately 18 hours. after incubation, the blood agar turns a reddish-brown color due to the α-hemolytic activity of this Enterococcus strain. If a compound inhibits the growth of this strain, a localized highly visible red zone results due to inhibition of hemolysis. This procedure allows for correlation of the desired biological activity with the appropriate chromatographic fractions, which in turn accelerates the identification of active principals and their isolation.

Adapting this procedure for use with the MREF assay involved testing of two different contrast agents. The first was 2,3, 5-triphenyl-2H-tetrazolium chloride OR (0.003% final) supplemented to 200 mL of Todd Hewitt agar medium. The second was the 0.5% sheep's blood supplemented to 200 mL of Mueller-Hinton agar medium. Both procedures showed definitive zones of growth inhibition, but the resolution was better and the incubation time was shorter with the blood agar medium. A range of cell inoculums were tested but $1 \times 10^6$ cells/ml gave the best results.

Isolation and Structural Characterization

The purification of nocathiacin antibiotics from Nocardia sp. fermentations was monitored using a multiple drug resistant *Enterococcus faecium* (MREF) agar diffusion assay. Extraction with ethyl acetate, followed by solvent partitioning, Sephadex LH-20 and/or silica gel chromatography were carried out. These steps yielded a complex of nocathiacin antibiotics which showed activity in the MREF agar diffusion assay. Final purification of the individual nocathiacin antibiotics was accomplished by normal or reverse phase preparative HPLC. Spectral data indicated that the compounds are in the thiazolyl peptide class of antibiotics. The structures of nocathiacin I, II and III (shown below) were assigned based on 2D NMR studies and positive ion electrospray HRMS and MS/MS data.

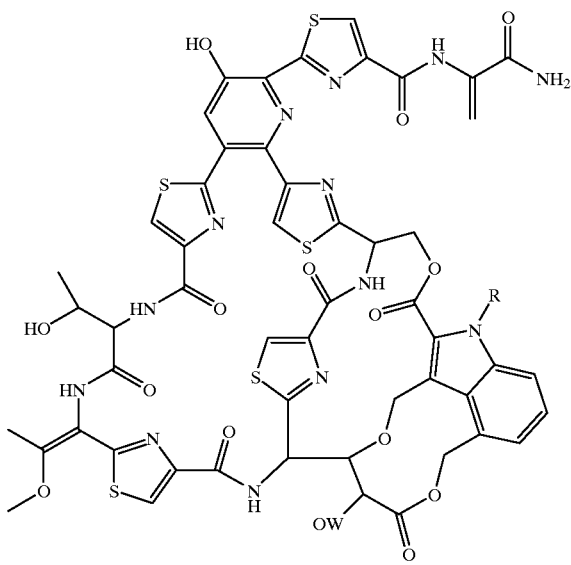

wherein W is

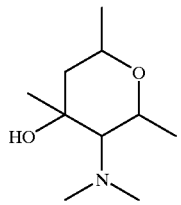

and R is OH (for nocathiacin I) or R is H (for nocathiacin II); and W is H and R is OH (for nocathiacin III).

General Methods

Materials:

Hexanes, chloroform, (anhydrous ACS grade), and methanol, acetonitrile (anhydrous HPLC grade) were obtained from the Fisher Scientific Company. These solvents were not repurified or redistilled. Water used in chromatography experiments refers to in-house deionized water passed through a Millipore 4 cartridge reagent grade water system (10 mega ohm Milli-Q water). Sephadex LH-20 was from Pharmacia LKB, Uppsala, Sweden. Dicalite (diatomaceous earth) was manufactured by Grefco Minerals, Torrance, Calif. LiChroprep Si 60, 25–40 µm was from EM Separations, NJ, a U.S. associate of E. Merck, Germany.

Analytical Thin Layer Chromatography (TLC)

Uniplate Silica Gel GHLF precoated thin layer chromatography plates (scored 10×20 cm, 250 microns) were purchased from Analtech, Inc., Newark, Del. Fractions were spotted using size 2 microliter Microcaps (disposable pipets) and the plates were developed in a tank equilibrated with chloroform-methanol (9:1 v/v). The components of the resulting chromatogram were visualized by long wavelength UV light and/or ceric sulfate-sulfuric acid spray reagent followed by prolonged heating.

Analytical HPLC

The purification of the nocathiacin antibiotics was monitored by HPLC analysis on an APEX 5µ ODS column, 4.6 mm i.d.×15 cm l. (product of Jones Chromatography Inc., Lakewood, Colo.). Analyses were done on a Hewlett Packard 1100 Series Liquid Chromatograph, with UV detection at 254 nm. A gradient system of acetonitrile and 0.01M potassium phosphate buffer pH 3.5 was used, according to the method of D. J. Hook et.al. (*J. Chromatogr.* 385, 99 (1987). The eluant was pumped at a flowrate of 1.2 ml/min.

Preparative HPLC

The following components were used to construct a preparative HPLC system: Beckman Instruments Inc. (Somerset, N.J.), Beckman "System Gold" 126 Programmable Solvent Module; Beckman 166 Programmable Detector Module; Beckman "System Gold" Version 711U software; IBM PS/2 55SX System Controller; YMC Inc. (Wilmington, N.C.) Preparative HPLC column (normal phase): PVA-Sil 5µ particle size, 120 Å pore size, 20 mm i.d.×150 mm l., fitted with a Diol 25µ particle size, 120 Å pore size, 10 mm i.d.×10 mm l. drop-in guard module); mobile phase chloroform—methanol gradient, flow rate 10 ml/min. UV detection: 290 nm. Alternative column (reverse phase): YMC Inc. ODS-AQ 5µ particle size, 120 Å pore size, 20 mm i.d.×150 mm l., fitted with a ODS-A 25µ particle size, 120 Å pore size, 10 mm i.d.×10 mm l. drop-in guard module); mobile phase 0.1M ammonium acetate—acetonitrile gradient; flow rate 10 ml/min. UV detection: 360 nm.

Analytical Instrumentation

Low resolution MS measurements were performed with a Finnigan SSQ 7000 single quadrupole mass spectrometer, using the positive electrospray ionization mode. MS/MS measurements were conducted in the positive electrospray ionization mode with a Finnigan TSQ 7000 tandem quadrupole mass spectrometer using Argon collision gas or a Finnigan LCQ ion trap mass spectrometer. High resolution MS data were determined with a Finnigan MAT 900 magnetic sector mass spectrometer, positive electrospray ionization mode, ppg reference. The UV spectra were obtained using a Hewlett-Packard 8452A diode array spectrophotometer. IR measurements were taken on a Perkin Elmer 2000 Fourier Transform spectrometer. $^1$H-NMR and $^{13}$C-NMR spectra were obtained on a Bruker DRX-500 instrument operating at 500.13 and 125.76 MHz, respectively, using a Nalorac microprobe. Chemical shifts are reported in parts per million (ppm) relative to solvent (DMSO-$d_6$, $\delta_H$ 2.49; $\delta_C$ 39.6). CD data were recorded with a Jasco J-720 spectropolarimeter.

EXAMPLES

The following examples set out the preparation of nocathiacin antibiotics and their biological properties. Reasonable variations, such as those which would occur to a skilled artisan can be made herein without departing from the scope of the invention.

FERMENTATION AND PURIFICATION OF NOCATHIACIN I & II

Nocathiacin I & II Preparation by Fermentation:

From the frozen vegetative stock culture of Nocardia sp. ATCC 202099, 4 ml was used to inoculate 100 ml of seed medium containing the following per liter of deionized water: starch, 20 g; Dextrose, 5 g; N-Z case, 3 g; yeast extract, 2 g; fish meat extract, 5 g; calcium carbonate, 3 g, in a 500-ml flask. The culture was incubated at 32° C. on a rotary shaker operating at 250 rpm for 3 days., Four ml of the resulting culture was used to inoculate each of two hundred 500-ml flasks containing 100 ml of production medium consisting of the following per liter of deionized water: Dextrose, 20 g; peptone, 5 g; Red Star yeast, 10 g; Allophosite, 5 g. The production cultures were incubated at 32° C. on a rotary shaker operating at 250 rpm for 5 days. The cultures were then processed for the recovery of nocathiacin I & II.

Example 1

From Fermentation in Shake Flasks

Preparation of Crude Extract A:

Fermentation broth of Nocardia sp. ATCC-202099 (20 L.) was extracted (whole broth including mycelia) with approximately 8 L. ethyl acetate by vigorous stirring for ½ hour. The biphasic mixture was mixed with approximately 3 L. (1 Kg) of dicalite and filtered by vacuum filtration using a large Coors Buchner funnel (27 cm i.d., 28.5 cm o.d., 9 cm deep). The pale yellow ethyl acetate layer was separated and evaporated in vacuo to dryness in a rotary evaporator to yield approximately 7.2 g of Residue A.

Liquid-Liquid Partition of Residue A:

Residue A (7.2 g) was dissolved in 100 ml of 10% water in methanol. The solution was transferred to a separatory funnel and extracted 4 times with an equal volume of hexane. The hexane layer was removed. The aqueous methanol phase was diluted to 35% water in methanol by adding 38 ml of water and extracted 3 times with an equal volume of chloroform. The chloroform had been previously saturated with 35% water in methanol. The hexane, chloroform, and aqueous methanol extracts were evaporated to dryness in vacuo in a rotary evaporator. The nocathiacin antibiotics were concentrated primarily in the chloroform fraction, (Residue B, 1.3 g).

Sephadex LH-20 Chromatography of Residue B:

Residue B (1.3 g) was dissolved in 10 ml chloroform-methanol 1:1 and applied to a 3×100 cm Glenco column packed with 100 g Sephadex LH-20 in chloroform-methanol 1:1. After a 75 ml forerun, fractions measuring 8–10 ml each were collected at a flow rate of 2–3 ml/min. Fractions were consolidated on the basis of silica TLC profiles (chloroform-methanol 9:1, long wavelength UV and/or ceric sulfate spray). In this manner, the yellow fluorescent nocathiacin antibiotic complex was detected in fractions 10–15. The fractions were combined and evaporated to dryness, (Residue C, 284 mg).

Silica Gel Vacuum Liquid Chromatography of Residue C:

The nocathiacin antibiotic enriched fraction (Residue C) was preadsorbed onto 2 g Merck LiChroprep Silica Gel 60 (25–40μ) and applied to a 2.5×15 cm fritted filter funnel packed half full with this adsorbent. Elution using house vacuum was initially with hexane-chloroform 1:1 (100 ml), followed by chloroform, and increasing percentages of methanol in chloroform (e.g. 2.5, 5, 7.5, 10, 12.5, 15, and 25% methanol in chloroform (100 ml each). Fractions were consolidated on the basis of silica TLC profiles (chloroform-methanol 9:1, long wavelength UV and ceric sulfate spray). In this manner, nocathiacin I was detected in the 5% through 12.5% methanol in chloroform fractions. Nocathiacin II was detected in the 15% through 25% methanol in chloroform fractions. Like fractions were combined and evaporated to dryness, (Residue D, nocathiacin I, 230 mg), (Residue E, nocathiacin II, 49 mg.)

Isolation of Nocathiacin I and II:

Residues D and E were further purified using the specified Beckman System Gold preparative HPLC system. A typical sample injection size was 25–50 mg/50–100 μl DMSO. Elution was begun with chloroform with a pre-programmed concave gradient to chloroform-methanol 8:2 over a 30 minute period. Elution flow rate was 10 ml/min. Detection (UV) was at 290 nm. In this manner, nocathiacin I (17 min peak, 56 mg total yield) and nocathiacin II (19.5 min peak, 6.7 mg total yield) were obtained.

Purification Scheme

The following scheme depicts the purification of nocathiacin antibiotics:

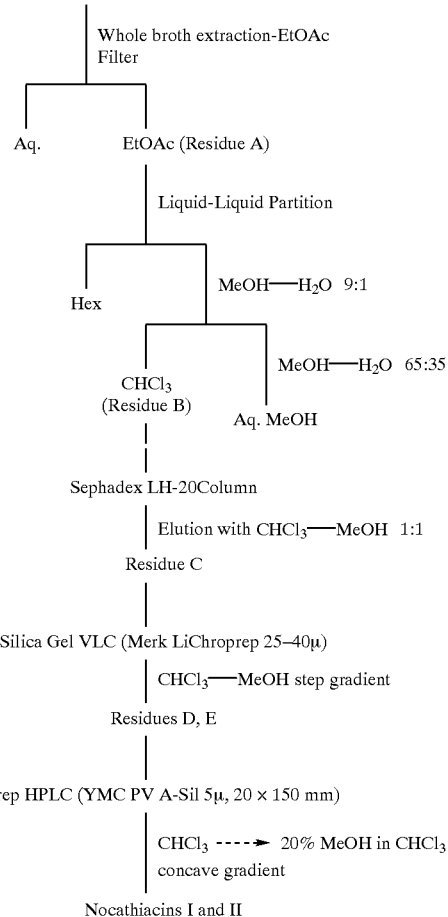

Physico-Chemical Properties of Nocathiacin I

Description: pale-yellow amorphous solid

Molecular Formula: $C_{61}H_{60}N_{14}O_{18}S_5$

Molecular Weight: 1436

Mass Spectrum: HR-ESIMS $[M+H]^+$ m/z 1437.285 ESI-MS/MS fragmentation ions: m/z 1266, 1248, 1221, 1204, 1186, 1154, 788

Infrared Spectrum: Major IR Bands ($cm^{-1}$) 3392, 3108, 2932, 1740, 1721, 1694, 1670, 1640, 1533, 1478, 1420, 1384, 1320, 1250, 1207, 1128, 1091, 1037, 1014, 751.

Ultraviolet Spectrum: $\lambda_{max}$ (MeOH) 222, 290, 364 nm (log ε 4.89, 4.52, 4.17)

Circular Dichroism: CD λ nm (Δε) (MeOH) 212 (+34.1), 239 (−50.5), 267 (+20.8), 307 (−8.7), 364 (+5.5)

HPLC (Rt) 25.6 min; (C18; Acetonitrile—0.01M potassium phosphate buffer pH 3.5 gradient (*J. Chromatogr.* 385, 99 (1987)).

¹H-NMR Observed Chemical Shifts (relative to DMSO-d₆ signal δ 2.49):

δ 10.05 (1H, s), 9.07 (1H, s), 8.65 (1H, s), 8.57 (1H, d, J=8.0 Hz), 8.51 (1H, s), 8.50 (1H, s), 8.24 (1H, s), 8.07 (1H, s br), 7.89 (1H, d, J=11.2 Hz), 7.86 (2H, s), 7.70 (1H, d, J=8.4 Hz), 7.61 (1H, s br), 7.34 (2H, m), 7.16 (1H, d, J=6.9 Hz), 6.40 (1H, s), 5.98 (1H, d, J=12.0 Hz), 5.77 (1H, s), 5.73 (1H, dd, J=10.9, 4.4 Hz), 5.70 (1H, d, J=8.7 Hz), 5.22 (1H, m), 5.02 (1H, d, J=11.4 Hz), 4.94 (1H, d, J=3.7 Hz), 4.75 (1H, d, J=10.2 Hz), 4.51 (1H, d, J=11.0 Hz), 4.29 (1H, d, J=9.6 Hz), 4.19 (1H, m), 4.13 (1H, d, J=10.1 Hz), 4.00 (1H, d, J=9.5 Hz), 3.88 (3H, s), 3.78 (1H, d br, J=5.9 Hz), 2.52 (6H, s), 2.49 (1H, m), 2.11 (1H, s br), 1.99 (3H, s), 1.95 (1H, m), 1.81 (1H, d, J=13.9 Hz), 1.43 (3H, s), 1.21 (1H, m), 1.16 (3H, s, br), 0.59 (3H, d, J=6.3 Hz).

¹³C-NMR Observed Chemical Shifts (relative to DMSO-d₆ signal δ 39.6):

δ 171.8, 168.1, 167.7, 167.4, 167.0, 165.2, 164.0, 163.1, 161.5, 161.1, 160.5, 160.3, 159.1, 158.6, 154.6, 151.9, 149.7, 149.6, 148.8, 145.8, 142.5, 135.3, 135.0, 134.5, 129.9, 128.1, 127.0, 126.3, 125.5, 124.0, 123.1, 119.8, 119.4, 112.7, 111.2, 109.7, 103.7, 95.1, 79.3, 70.6, 68.4, 67.5, 66.1, 65.1, 64.5, 63.3, 56.1, 55.5, 50.2, 49.8, 44.4, 40.0, 30.5, 18.0, 13.1.

Physico-Chemical Properties of Nocathiacin II

Description: pale-yellow amorphous solid
Molecular Formula: $C_{61}H_{60}N_{14}O_{17}S_5$
Molecular Weight: 1420
Mass Spectrum: HR-ESIMS [M+H]⁺ m/z 1421.297 ESI-MS/MS fragmentation ions: m/z 1250, 1206, 1188, 1170, 1156, 1138, 788
Infrared Spectrum: Major IR Bands (cm⁻¹) 3387, 1725, 1656, 1534, 1478, 1423, 1318, 1249, 1192, 1087, 1014, 886, 793, 751.
Ultraviolet Spectrum: $\lambda_{max}$ (MeOH) 220, 295, 364 nm (log ε 5.01, 4.67, 4.36)
Circular Dichroism: CD λ nm (Δε) (MeOH) 211 (+41.5), 235 (−56.1), 258 (+21.0), 277 (+13.4), 307 (−10.0), 364 (+5.6)
HPLC (Rt) 21.1 min; (C18; Acetonitrile—0.01M potassium phosphate buffer pH 3.5 gradient (*J. Chromatogr.* 385, 99 (1987)).

¹H-NMR Observed Chemical Shifts (relative to DMSO-d₆ signal δ 2.49):

δ 9.10 (1H, s), 8.59 (1H, d, J=8.5 Hz), 8.51 (1H, s), 8.45 (1H, s), 8.22 (1H, s), 8.15 (1H, s), 8.05 (1H, s br), 7.69 (1H, s br), 7.66 (1H, s), 7.51 (1H, d, J=8.3 Hz), 7.47 (1H, s), 7.30 (1H, s), 7.25 (1H, dd, J=8.0, 7.2 Hz), 7.12 (1H, d, J=7.1 Hz), 7.02 (1H, d, J=8.4 Hz), 6.49 (1H, s), 6.03 (1H, d, J=12.1 Hz), 5.78 (1H, m), 5.70 (1H, d, J=8.6 Hz), 5.66 (1H, s), 5.30 (1H, d, J=7.7 Hz), 5.00 (1H, d, J=13.0 Hz), 4.98 (1H, d, J=10.5 Hz), 4.94 (1H, d, J=4.8 Hz), 4.83 (1H, d, J=11.2 Hz), 4.72 (1H, m), 4.37 (1H, d, J=9.6 Hz), 4.23 (1H, m), 4.11 (1H, d, J=9.9 Hz), 4.03 (1H, d, J=7.7 Hz), 3.89 (3H, s), 3.75 (1H, m), 2.49 (6H, s), 2.14 (1H, m), 2.01 (3H, s), 1.94 (1H, m), 1.79 (1H, d, J=14.2 Hz), 1.40 (3H, s), 1.23 (1H, m), 1.04 (3H, s, br), 0.54 (3H, d, J=6.5 Hz).

¹³C-NMR Observed Chemical Shifts (relative to DMSO-d₆ signal δ 39.6):

δ 172.0, 168.2, 167.1, 167.0, 165.5, 165.3, 163.2, 162.9, 161.6, 161.2, 160.6, 160.1, 158.7, 156.3, 149.9, 149.0, 148.2, 145.9, 138.8, 136.9, 134.3, 128.8, 127.9, 127.2, 126.6, 125.6, 125.2, 124.7, 124.1, 123.9, 122.8, 117.9, 116.3, 115.6, 109.9, 101.9, 95.1, 79.0, 70.7, 68.4, 67.6, 66.3, 66.0, 64.0, 62.5, 56.1, 55.1, 51.4, 50.6, 44.4, 40.5, 30.6, 18.1, 18.0, 13.0.

BIOLOGICAL EVALUATION OF NOCATHIACIN ANTIBIOTICS

Example 2

Antibiotic Activity of Nocathiacin I and II

To demonstrate its antimicrobial properties, the minimum inhibitory concentration (MIC) for nocathiacin antibiotics of the invention was obtained against a variety of bacteria using a conventional broth dilution assay (serial broth dilution method using nutrient broth (Difco)). The results obtained are shown in Table 1 below, and demonstrate that nocathiacins have utility in treating bacterial infections.

TABLE 1

| Organism | Strain # | MIC (ug/ml) Nocathiacin I | MIC (ug/ml) Nocathiacin II |
|---|---|---|---|
| Streptococcus pneumoniae | A9585 | 0.001 | 0.015 |
| Streptococcus pneumoniae/penicillin intermediate | A27881 | 0.001 | 0.015 |
| Streptococcus pneumoniae/penicillin resistant | A28272 | 0.001 | 0.015 |
| Streptococcus pyogenes | A9604 | 0.001 | 0.125 |
| Enterococcus faecalis | A20688 | 0.03 | 0.5 |
| Enterococcus faecalis | A27519 | 0.03 | 0.5 |
| Enterococcus faecalis + 50% calf serum | A20688 | 0.25 | 0.5 |
| Enterococcus faecium | A24885 | 0.015 | 0.5 |
| Enterococcus faecium/thiostrepton resistant (10 ug/ml) | SC15829 | 0.125 | 0.5 |
| Enterococcus avium | A27456 | 0.015 | 0.5 |
| Staphylococcus aureus | A9537 | 0.001 | 0.06 |
| Staphylococcus aureus/β-lactamase positive | A15090 | 0.007 | 0.5 |
| Staphylococcus aureus + 50% calf serum | A15090 | 0.015 | 0.5 |
| Staphylococcus aureus/QC/ATCC#29213 | A24407 | 0.007 | 0.5 |
| Staphylococcus aureus /hetero methicillin resistant | A27218 | 0.003 | 0.5 |
| Staphylococcus aureus + 50% calf serum | A27218 | 0.007 | 0.5 |
| Staphylococcus aureus /homo methicillin resistant | A27223 | 0.003 | 0.125 |
| Staphylococcus aureus + 50% calf serum | A27223 | 0.001 | 0.125 |
| Micrococcus luteus | A9852 | 0.003 | 0.125 |
| Bacillus subtilis | A9506A | 0.001 | 0.125 |
| Staphylococcus epidermidis | A24548 | 0.003 | 0.125 |
| Staphylococcus haemolyticus | A27298 | 0.03 | 0.25 |
| Escherichia coli | A15119 | >128 | >128 |
| Escherichia coli | A22292 | >128 | >128 |
| Escherichia coli/AcrA::Kan | A28901 | >128 | >128 |
| Salmonella enteritidis | A9531 | >128 | >128 |
| Moraxella catarrhalis/β-lactamase positive | A22344 | 0.06 | 0.125 |
| Moraxella catarrhalis/β-lactamase positive | A25409 | 0.06 | 0.125 |
| Haemophilus influenzae/β-lactamase negative | A20191 | >128 | |
| Haemophilus influenzae/β-lactamase negative | A20183 | >128 | |
| Haemophilus influenzae/β-lactamase positive | A21515 | >128 | |
| Salmonella/WT | A27207 | >128 | >128 |
| Salmonella/RE | A27208 | >128 | >128 |

Example 3

Nocathiacin I in vivo Antibiotic Activity in a Systemic *Staph. aureus* Infection Model Nocathiacin I was evaluated for antibiotic activity in vivo, in a systemic infection model using female ICR mice. The animals were infected IP with $6.5 \times 10^6$ CFU of an overnight culture of *Staphylococcus aureus* A15090 suspended in 7% mucin. Nocathiacin I was dissolved in a test formulation consisting of 10% DMSO, 5% Tween 80 and 85% water. The solution was administered subcutaneously at 100 mg/kg total dose (2×50 mg/kg doses at 1 and 4 hours post-infection). Nine out of nine animals survived the duration of the experiment with no signs of toxicity. The $PD_{50}$ of nocathiacin I was determined to be <6.25 mg/kg.

NOCATHIACIN III PREPARED BY FERMENTATION

Production of nocathiacin III can be effected at any temperature conducive to satisfactory growth of the producing organism, e.g. 16° C. and 40° C., but it is preferable to conduct the fermentation at 22° C. to 26° C. The aqueous medium is incubated for a period of time necessary to complete the production of nocathiacin III as monitored by high pressure liquid chromatography (HPLC) usually for a period of about 1–5 days, on a rotary shaker operating at about 50 rpm to 300 rpm, preferably at 150 to 200 rpm.

The product, nocathiacin III, can be recovered from the culture medium by conventional means which are commonly used for the recovery of other known biologically active substances. Nocathiacin III can be obtained upon extraction of the culture with a conventional solvent, such as ethyl acetate, treatment with a conventional resin (e.g. anion or cation exchange resin, non-ionic adsorption resin), treatment with a conventional adsorbent (e.g. activated charcoal, silica gel, cellulose, alumina), crystallization, recrystallization, and/or purification by reverse phase preparative HPLC.

The following examples set out the preparation of nocathiacin III by fermentation. Reasonable variations, such as those which would occur to a skilled artisan can be made herein without departing from the scope of the invention.

Fermentation
Example 4

From the frozen vegetative stock culture of Nocardia sp. ATCC-202099, 4 ml was used to inoculate 100 ml of seed medium contained the following per liter of deionized water: Japanese soluble starch, 20 g; Dextrose, 5 g; N-Z case, 3 g; yeast extract, 2 g; fish meat extract, 5 g; calcium carbonate 3 g, in a 500-ml flask. The culture was incubated at 28° C. on a rotary shaker operating at 250 rpm for 3 days. Four ml of the resulting culture was used to inoculate each of ten 500-ml flasks containing the 100 ml of producing medium consisting of the following per liter of deionized water: HY yeast 412, 10 g; Dextrose, 20 g; Nutrisoy, 10 g. The producing cultures were incubated at 28° C. on a rotary shaker operating at 250 rpm for 2 days. The cultures were then processed for the recovery of the nocathiacin III.

Example 5

From the frozen vegetative stock culture of Nocardia sp. ATCC-202099, 4 ml was used to inoculate 100 ml of seed medium contained the following per liter of deionized water: Japanese soluble starch, 20 g; Dextrose, 5 g; N-Z case, 3 g; yeast extract, 2 g; fish meat extract, 5 g; calcium carbonate 3 g, in a 500-ml flask. The culture was incubated at 28° C. on a rotary shaker operating at 250 rpm for 3 days. Four ml of the resulting culture was added to each of five 500-ml flasks containing the 100 ml of fresh seed medium and the culture was incubated at 28° C. on a rotary shaker operating at 250 rpm for 3 days. The resulting culture from five flasks was pooled and 4 ml of the combined culture was used to inoculate each of one hundred 500-ml flasks containing the 100 ml of producing medium consisting of the following per liter of deionized water: HY yeast 412, 10 g; Dextrose, 20 g; Nutrisoy, 10 g. The producing cultures were incubated at 24° C. on a rotary shaker operating at 180 rpm for 4 days. The cultures were then processed for the recovery of the nocathiacin III.

Example 6

Isolation of Nocathiacin III

Preparation of Crude Extract:

Fermentation broth of Nocardia sp. ATCC-202099 (1.2 L.) was extracted (whole broth including mycelia) with approximately 1 L. ethyl acetate by vigorous shaking. The biphasic mixture was centrifuged and the phases separated. The aqueous portion was extracted again with ethyl acetate (0.5 L.). The pale yellow ethyl acetate extracts were pooled and evaporated in vacuo to dryness in a rotary evaporator to yield approximately 198 mg of Residue A.

Liquid-Liquid Partition of Residue A

Residue A (198 mg) was dissolved in 10 ml of 10% water in methanol. The solution was transferred to a separatory funnel and extracted 3 times with an equal volume of hexane. The hexane layer was removed. The aqueous methanol phase was diluted to 35% water in methanol by adding 3.8 ml of water and extracted 3 times with an equal volume of chloroform. The chloroform had been previously saturated with 35% water in methanol. The hexane, chloroform, and aqueous methanol extracts were evaporated to dryness in vacuo in a rotary evaporator. Nocathiacin antibiotics were detected primarily in the chloroform fraction, (Residue B 106 mg).

Isolation of Nocathiacin III:

Residue B was further purified using the specified Beckman System Gold preparative HPLC system; YMC ODS-AQ C18 column. A typical sample injection size was 50 mg/250 µl DMSO. Elution was begun with 0.1M ammonium acetate-acetonitrile 55:45 v/v with a 30 minute linear gradient to acetonitrile. Elution flow rate was 10 ml/min. Detection (UV) was at 360 nm. In this manner, nocathiacin III (9 minute peak, 12 mg total yield) was obtained.

Physico-Chemical Properties of Nocathiacin III

Description: buff amorphous solid
Molecular Formula: $C_{52}H_{43}N_{13}O_{16}S_5$
Molecular Weight: 1265
Mass Spectrum: HR-ESIMS $[M+H]^+$ m/z 1266.162 ESI-MS/MS fragmentation ions: m/z 1248, 1222, 1204, 1186, 788
Infrared Spectrum: Major IR Bands ($cm^{-1}$) 3382, 1720, 1667, 1643 sh, 1534, 1510, 1477, 1420, 1250, 1207, 1126, 1015, 750.
Ultraviolet Spectrum: $\lambda_{max}$ (MeOH) nm 224, 290, 364 (log ε 4.85, 4.52, 4.11).
Circular Dichroism: CD λ nm (Δε) (MeOH) 212 (+38.7), 238 (−47.6), 266 (+21.2), 305 (−11.4), 362 (+5.1).
HPLC (Rt) 19.3 min; (C18; Acetonitrile—0.01M potassium phosphate buffer pH 3.5 gradient (*J. Chromatogr.* 385, 99 (1987)).
$^1$H-NMR Observed Chemical Shifts (relative to DMSO-$d_6$ signal δ 2.49):

δ 10.05 (1H, s), 8.93 (1H, s), 8.59 (1H, s), 8.51 (1H, s), 8.46 (1H, s), 8.37 (1H, d, J=8.9 Hz), 8.20 (1H, s), 8.05 (1H, s), 7.91 (1H, d, J=10.9 Hz), 7.77 (1H, s br), 7.74 (1H, s br), 7.69 (1H, d, J=8.4 Hz), 7.60 (1H, s), 7.38

(1H, d, J=7.5 Hz), 7.34 (1H, dd, J=8.2, 7.2 Hz), 7.18 (1H, d, J=7.0 Hz), 6.37 (1H, s), 6.07 (1H, d, J=7.1 Hz), 5.92 (1H, d, J=12.2 Hz), 5.89 (1H, d, J=10.3 Hz), 5.74 (1H, dd, J=10.8, 4.8 Hz), 5.72 (1H, s), 5.24 (1H, m), 5.02 (1H, d, J=12.5 Hz), 4.71 (1H, d, J=10.4 Hz), 4.54 (1H, d, J=11.2 Hz), 4.50 (1H, m), 4.20 (1H, m), 4.13 (1H, d, J=10.4 Hz), 4.02 (1H, dd, J=9.4, 7.2 Hz), 3.87 (3H, s), 3.73 (1H, d, J=9.6 Hz), 1.97 (3H, s), 1.15 (3H, s br).

$^{13}$C-NMR Observed Chemical Shifts (relative to DMSO-d$_6$ signal δ 39.6):

δ 174.5, 172.2, 168.1, 167.8, 166.6, 165.3, 164.4, 163.0, 161.2, 160.4, 159.3, 158.8, 154.7, 152.9, 149.6, 148.8, 146.0, 141.6, 135.7, 135.0, 134.5, 129.9, 128.6, 127.1, 126.4, 126.3, 125.6, 125.3, 124.2, 123.1, 119.7, 119.5, 112.5, 111.3, 109.8, 103.7, 81.4, 67.9, 67.3, 65.3, 64.5, 63.5, 56.2, 55.7, 49.7, 49.5, 18.0, 13.2.

Example 7

Antibiotic Activity of Nocathiacin III

To demonstrate its antimicrobial properties, the minimum inhibitory concentration (MIC) for the nocathiacin III antibiotic of this invention was obtained against a variety of bacteria using a conventional broth dilution assay (serial broth dilution method using nutrient broth (Difco)). The results obtained are shown in Table 2 below, and demonstrate that nocathiacin III has utility in treating bacterial infections.

TABLE 2

| Organism | Strain # | MIC (ug/ml) Nocathiacin III |
| --- | --- | --- |
| Streptococcus pneumoniae | A9585 | ≦0.002 |
| Streptococcus pneumoniae/penicillin intermediate | A27881 | ≦0.002 |
| Streptococcus pneumoniae/penicillin resistant | A28272 | ≦0.002 |
| Enterococcus faecalis | A20688 | 0.03 |
| Enterococcus faecalis | A27519 | 0.03 |
| Enterococcus faecalis + 50% calf serum | A20688 | 0.25 |
| Enterococcus faecium | A24885 | 0.03 |
| Enterococcus avium | A27456 | 0.03 |
| Staphylococcus aureus/β-lactamase positive | A15090 | 0.007 |
| Staphylococcus aureus + 50% calf serum | A15090 | 0.03 |
| Staphylococcus aureus/QC/ATCC#29213 | A24407 | 0.007 |
| Staphylococcus aureus /homo methicillin resistant | A27223 | 0.007 |
| Staphylococcus aureus + 50% calf serum | A27223 | 0.007 |
| Staphylococcus epidermidis | A24548 | 0.007 |
| Staphylococcus haemolyticus | A27298 | 0.007 |
| Moraxella catarrhalis/β-lactamase positive | A22344 | 0.06 |
| Moraxella catarrhalis/β-lactamase positive | A25409 | 0.06 |
| Haemophilus influenzae/β-lactamase negative | A20191 | >64 |
| Haemophilus influenzae/β-lactamase negative | A20183 | >64 |
| Haemophilus influenzae/β-lactamase positive | A21515 | >64 |

What is claimed is:

1. A nocathiacin compound, or a pharmaceutically acceptable salt thereof having the formula

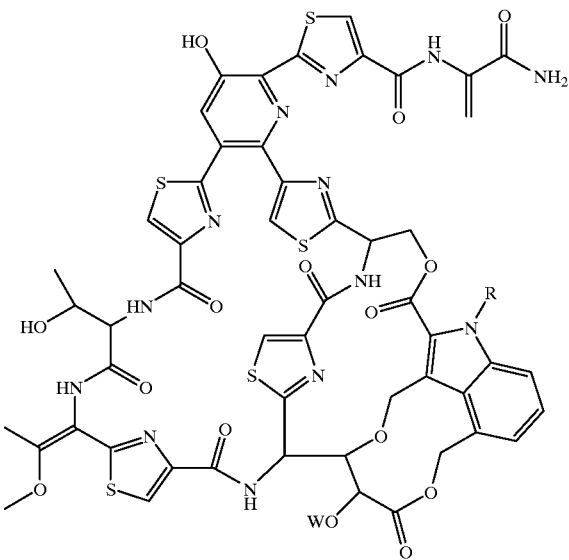

wherein:

R is H or OH;

W is H or

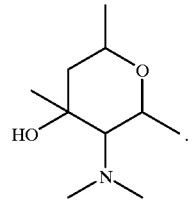

Figure 2:
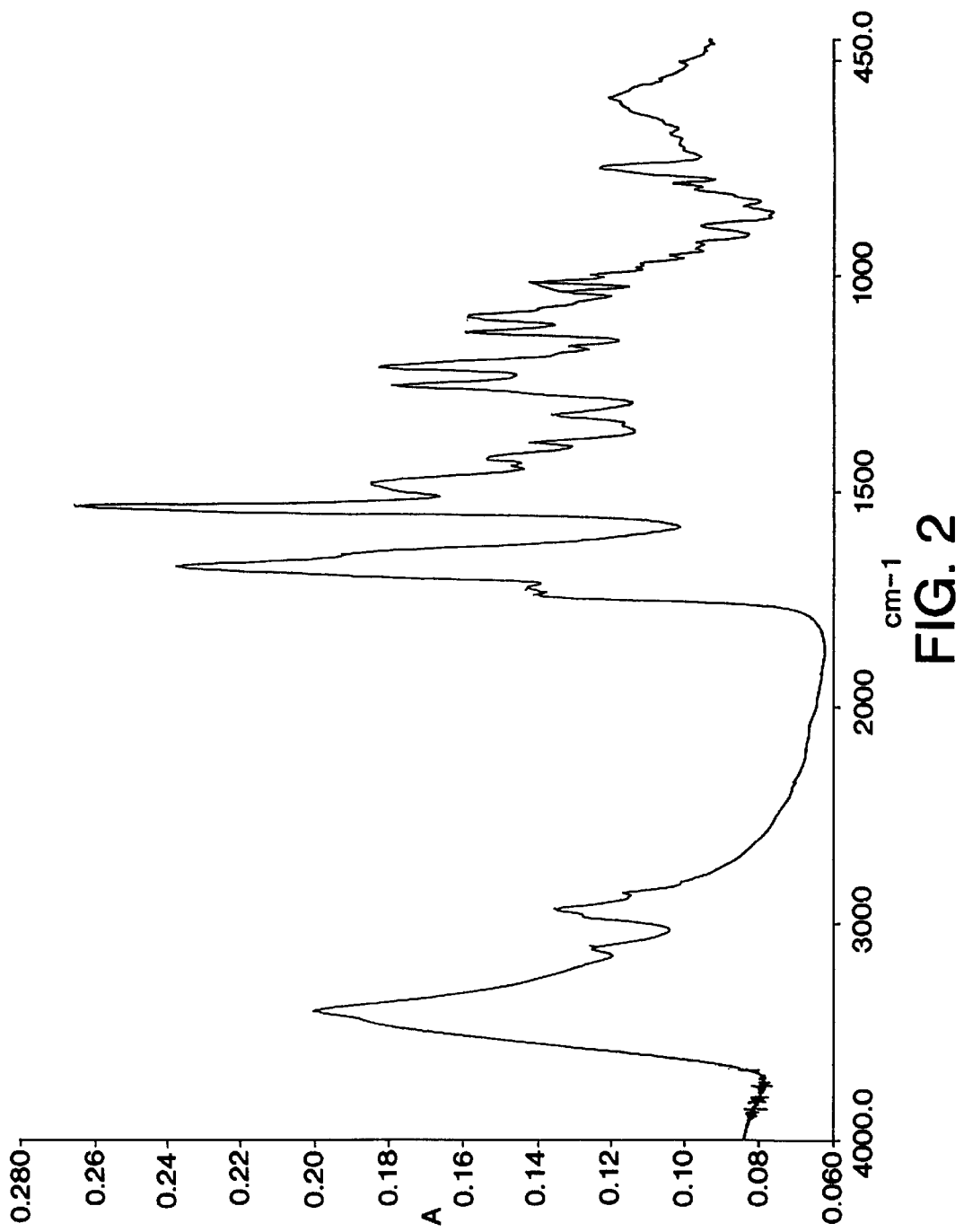
FIG. 2 shows the infrared absorption (IR) spectrum of nocathiacin I.
Figure 3:
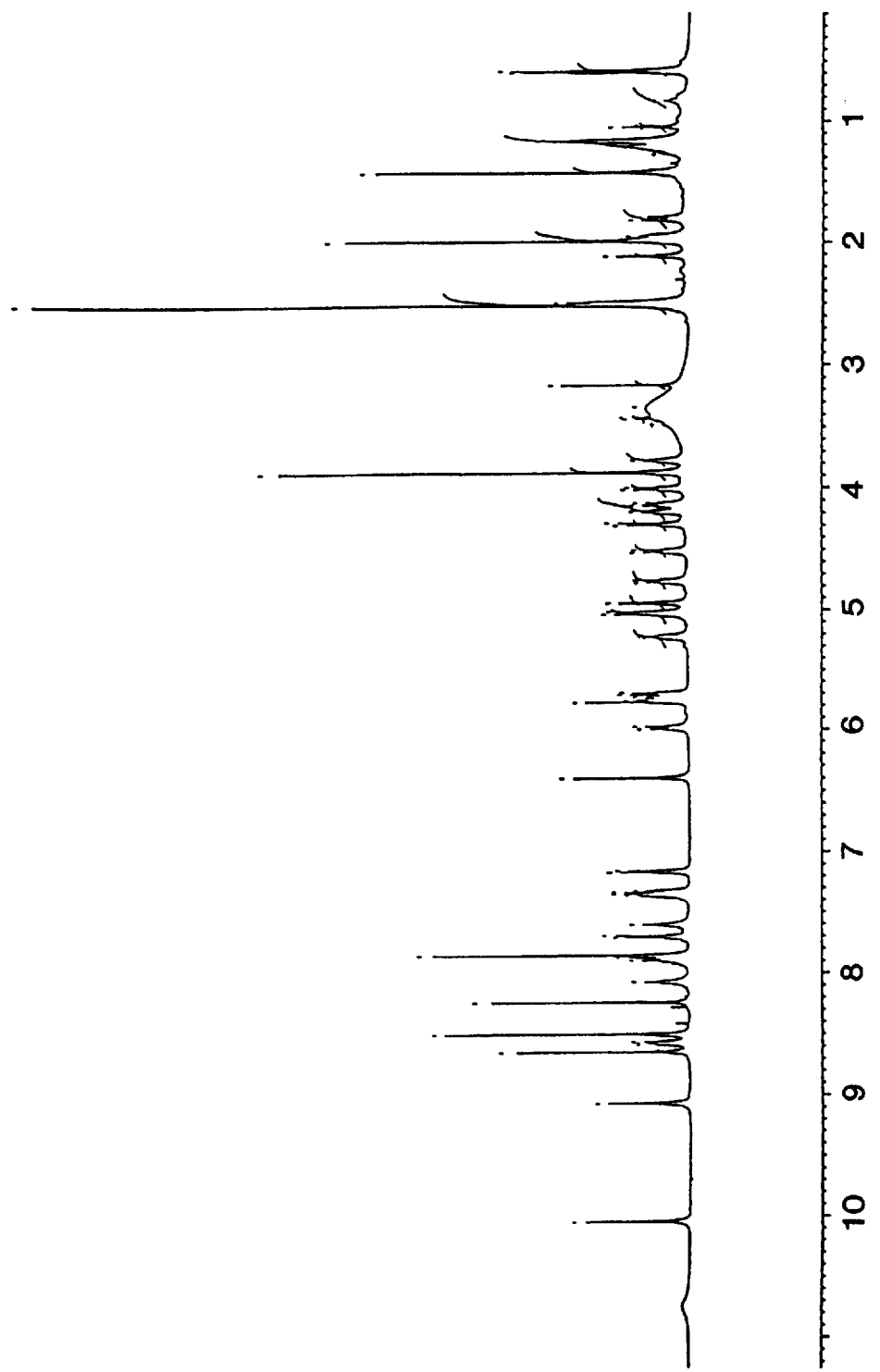
FIG. 3 shows the $^1$H-NMR spectrum (500 MHz) of nocathiacin I in deuterated dimethylsulfoxide.
Figure 4:
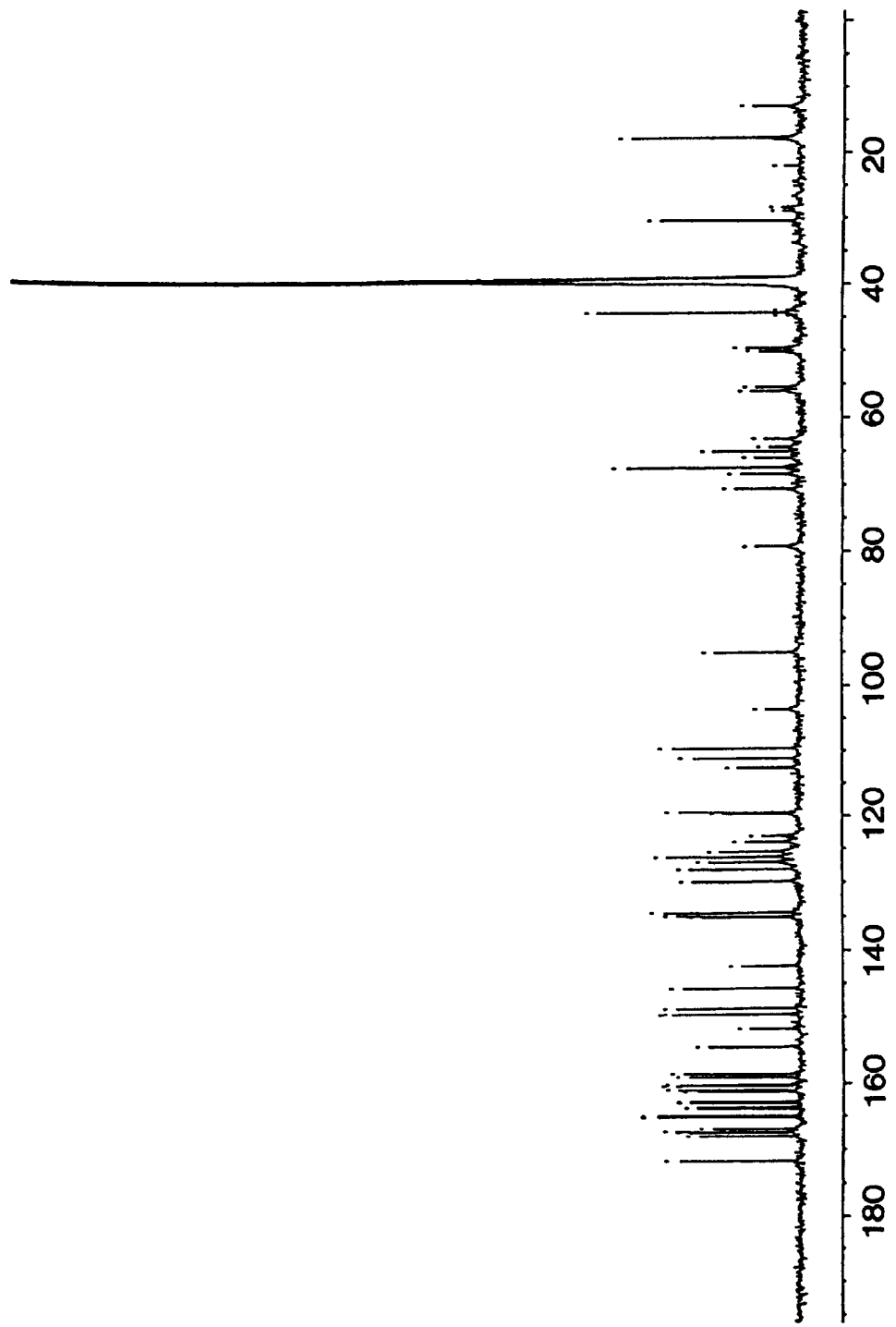
FIG. 4 shows the $^{13}$C-NMR (125 MHz) spectrum of nocathiacin I in deuterated dimethylsulfoxide.

2. The compound of claim 1 selected from the group consisting of nocathiacin I, II and III, or a pharmaceutically acceptable salt thereof;

wherein nocathiacin I has the following characteristics:

(a) appears as a pale-yellow amorphous solid;

(b) has a molecular weight of 1436 as determined by mass spectrometry;

(c) has the molecular formula $C_{61}H_{60}N_{14}O_{18}S_5$ (d) exhibits an ultraviolet absorption spectrum when dissolved in methanol substantially as shown in FIG. 1;

(e) exhibits an infrared absorption spectrum (KBr) substantially as shown in FIG. 2;

(f) when dissolved in deuterated dimethylsulfoxide exhibits a proton magnetic resonance spectrum substantially as shown in FIG. 3;

(g) when dissolved in deuterated dimethylsulfoxide exhibits a $^{13}$C magnetic resonance spectrum substantially as shown in FIG. 4;

(h) exhibits a high performance liquid chromatography retention time of 25.6 minutes with a C18 reversed phase silica gel column using a 0.01M potassium phosphate buffer pH 3.5—acetonitrile gradient;

(i) and has the formula

Figure 5:
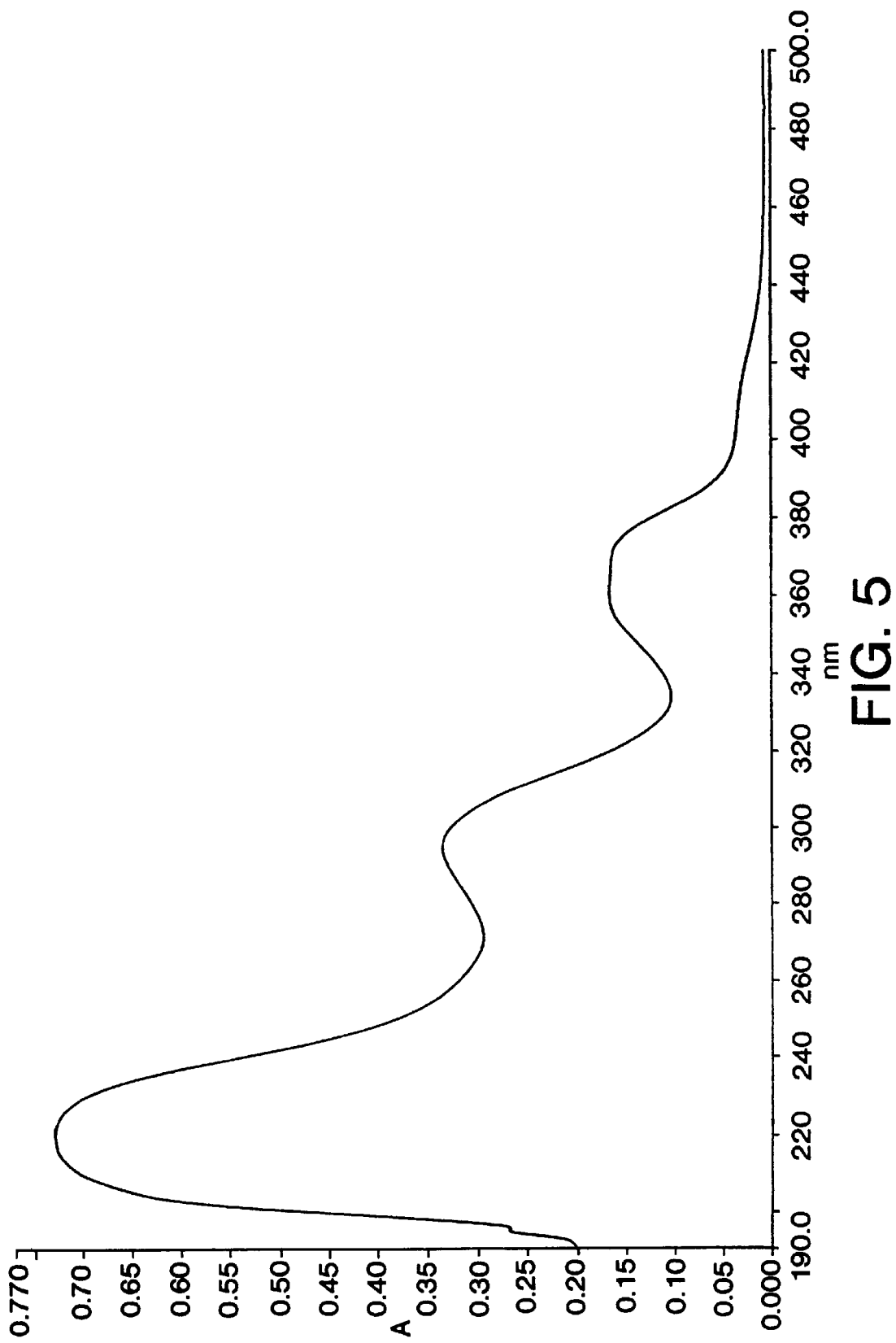
FIG. 5 shows the ultraviolet absorption (UV) spectrum of nocathiacin II.
Figure 6:
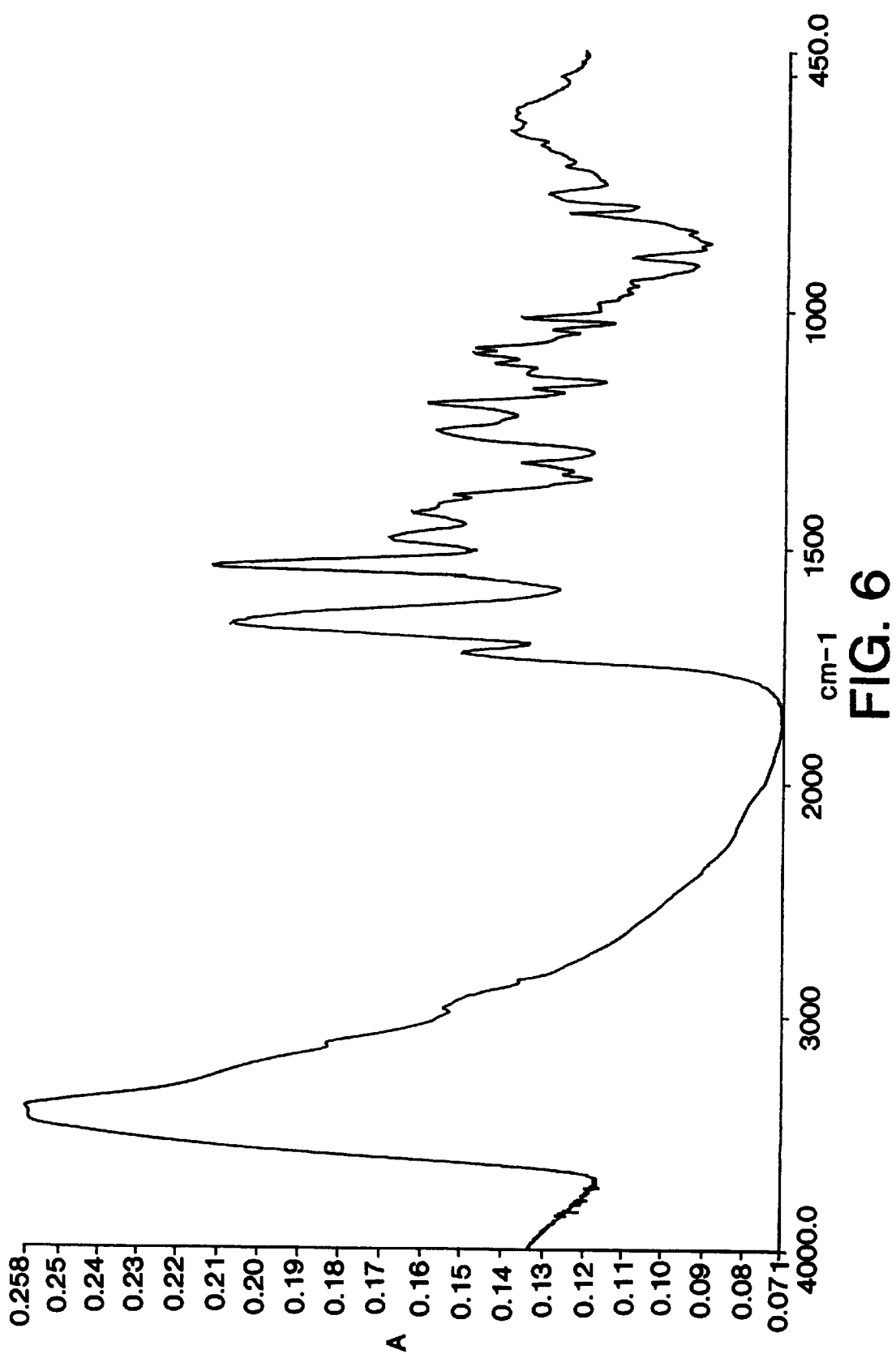
FIG. 6 shows the infrared absorption (IR) spectrum of nocathiacin II.
Figure 7:
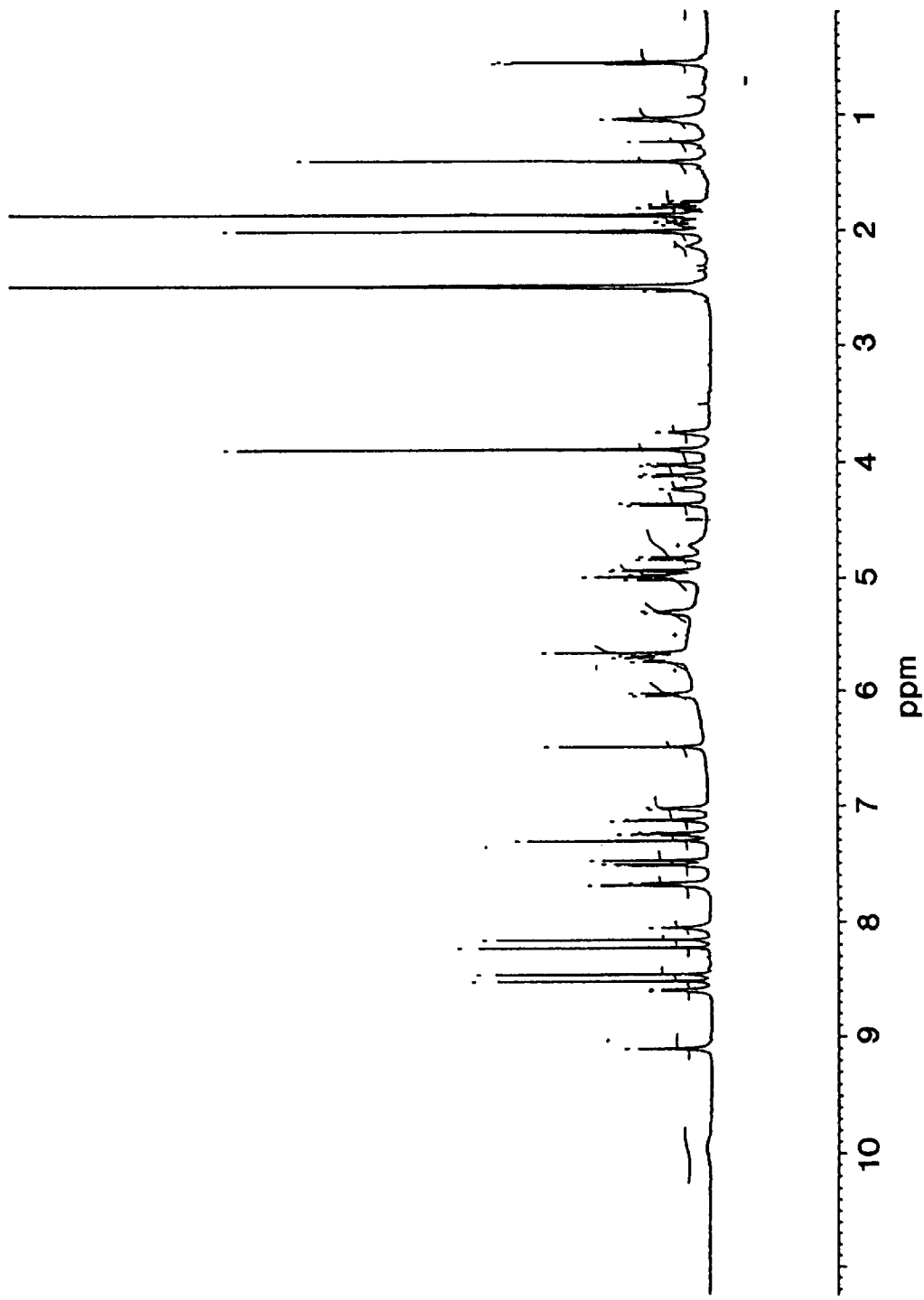
FIG. 7 shows the $^1$H-NMR spectrum (500 MHz) of nocathiacin II in deuterated dimethylsulfoxide.
Figure 8:
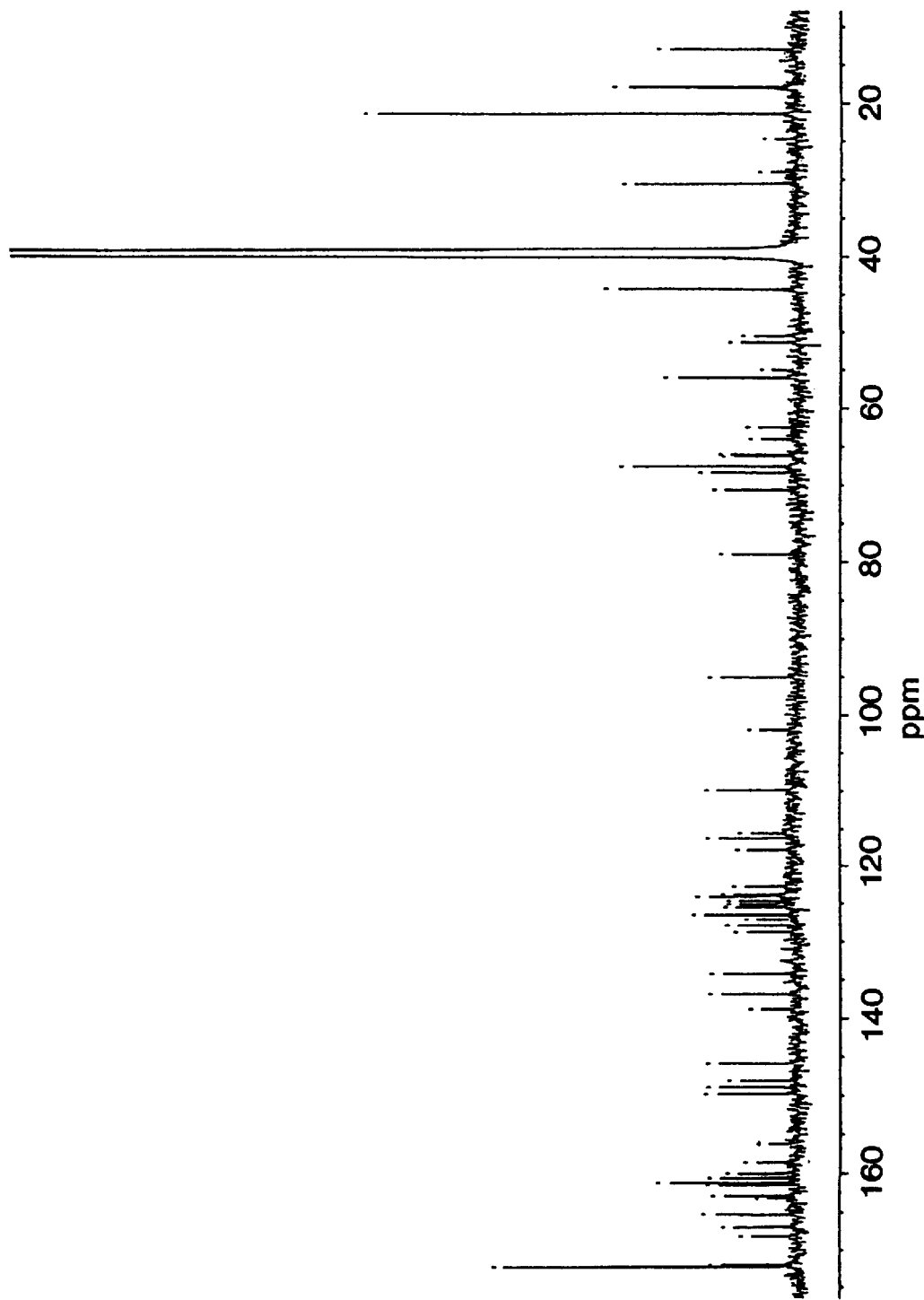
FIG. 8 shows the $^{13}$C-NMR (125 MHz) spectrum of nocathiacin II in deuterated dimethylsulfoxide.

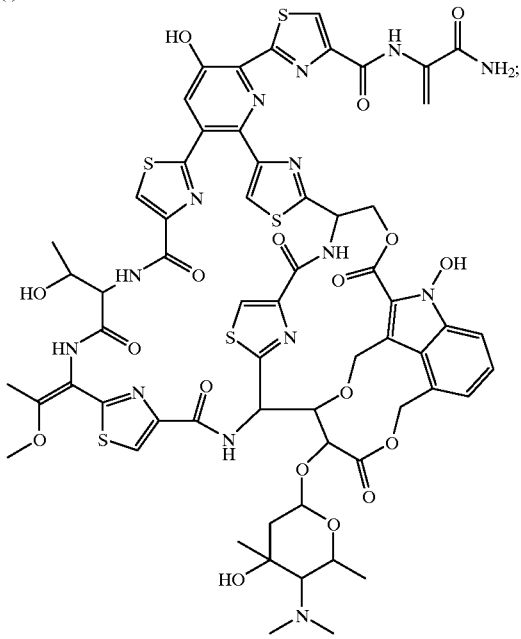

wherein nocathiacin II has the following characteristics:
(a) appears as a pale-yellow amorphous solid;
(b) has a molecular weight of 1420 as determined by mass spectrometry;
(c) has the molecular formula $C_{61}H_{60}N_{14}O_{17}S_5$
(d) exhibits an ultraviolet absorption spectrum when dissolved in methanol substantially as shown in FIG. 5;
(e) exhibits an infrared absorption spectrum (KBr) substantially as shown in FIG. 6;
(f) when dissolved in deuterated dimethylsulfoxide exhibits a proton magnetic resonance spectrum substantially as shown in FIG. 7;
(g) when dissolved in deuterated dimethylsulfoxide exhibits a $^{13}C$ magnetic resonance spectrum substantially as shown in FIG. 8;
(h) exhibits a high performance liquid chromatography retention time of 21.1 minutes with a C18 reversed phase silica gel column using a 0.01M potassium phosphate buffer pH 3.5—acetonitrile gradient;
(i) and has the formula

Figure 9:
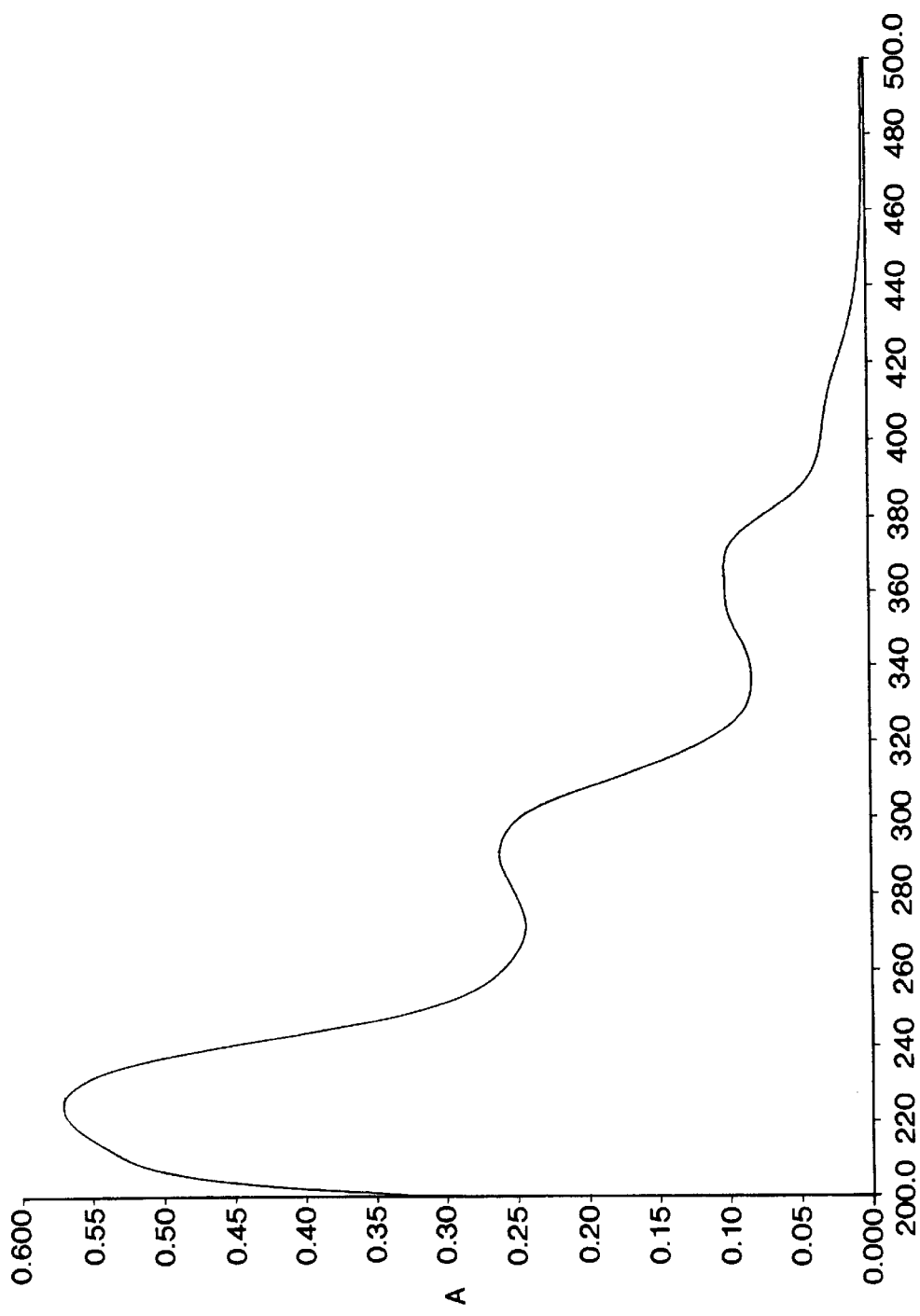
FIG. 9 shows the ultraviolet absorption (UV) spectrum of nocathiacin III.
Figure 10:
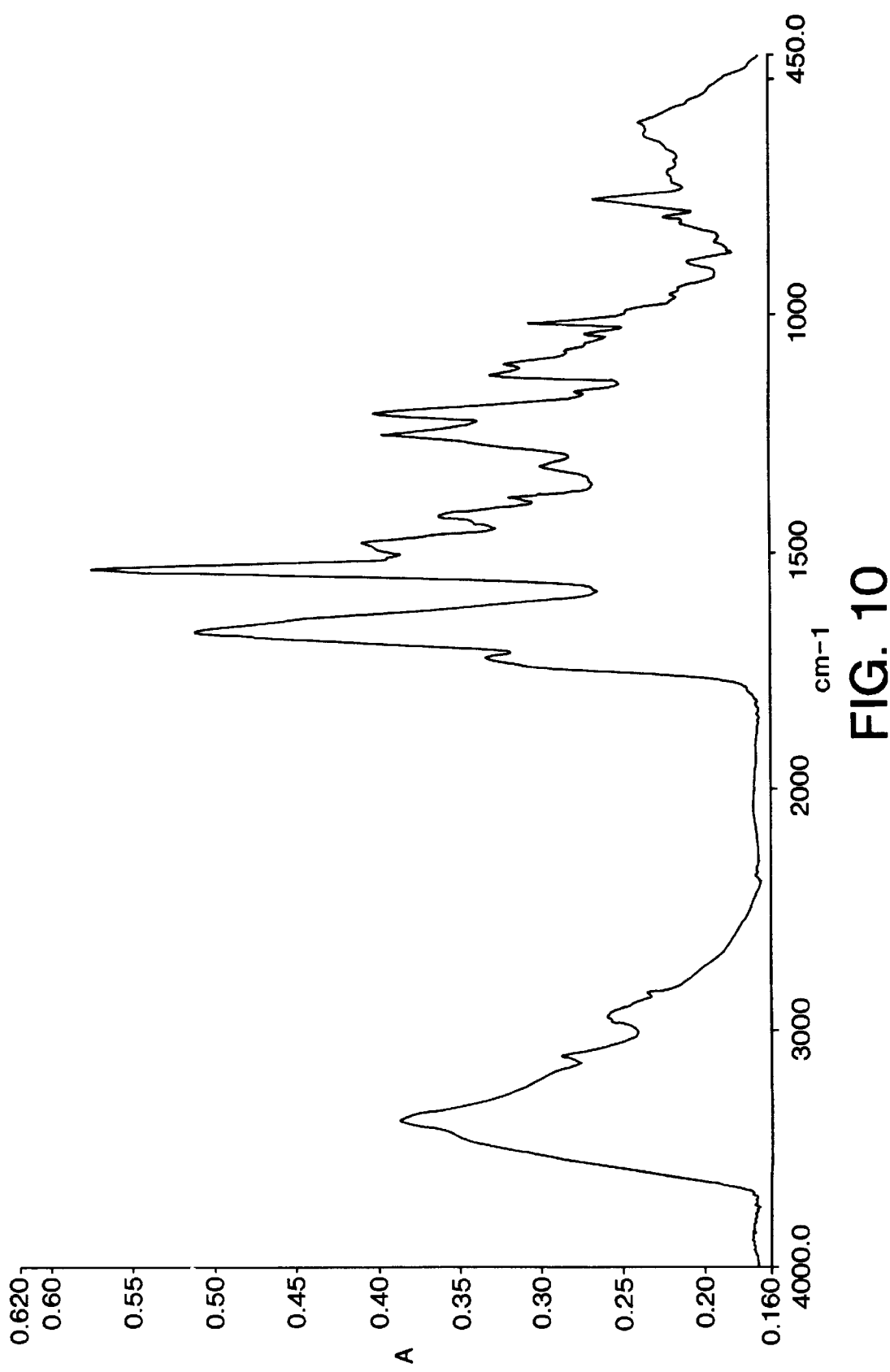
FIG. 10 shows the infrared absorption (IR) spectrum of nocathiacin III.
Figure 11:
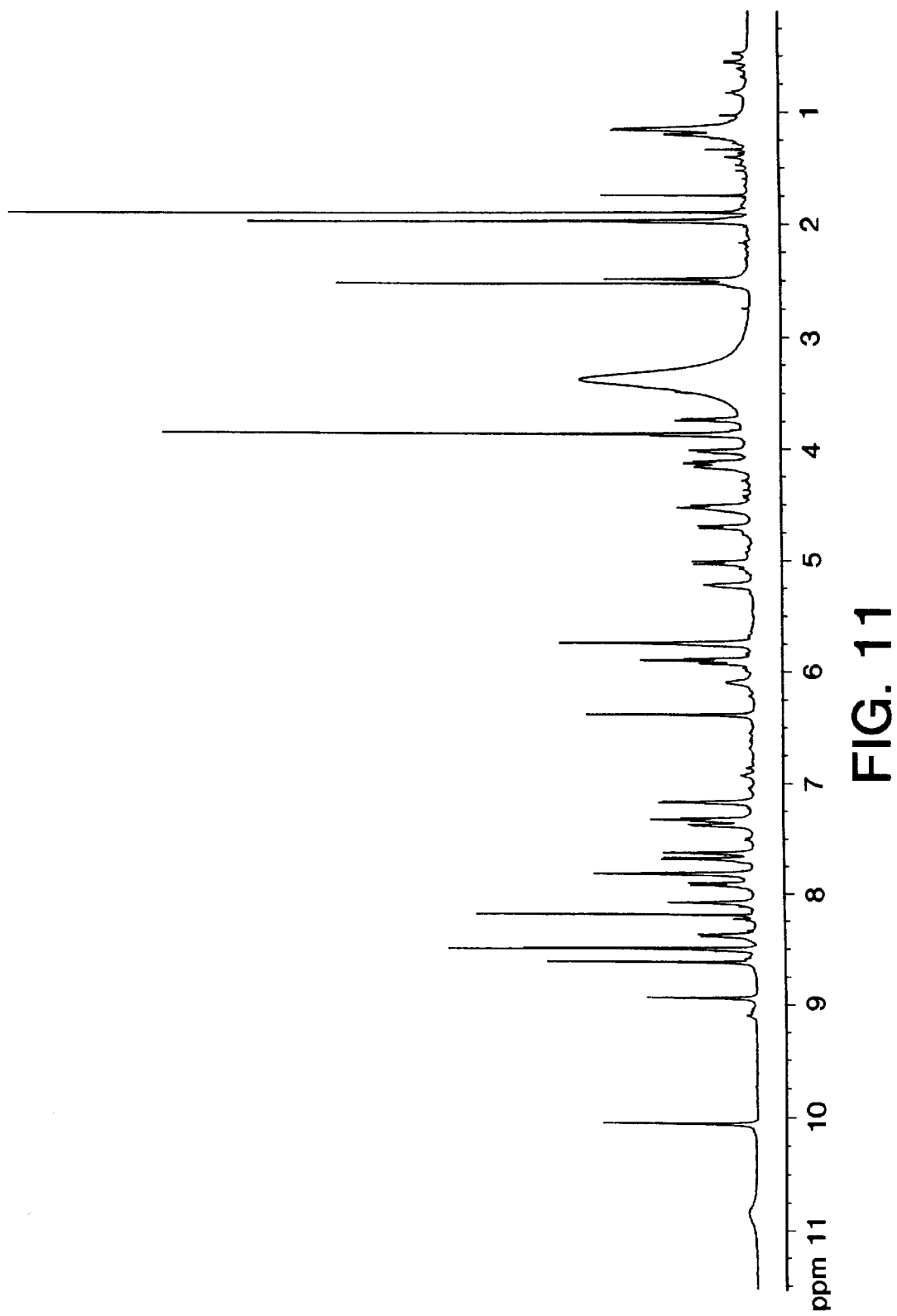
FIG. 11 shows the $^1$H-NMR spectrum (500 MHz) of nocathiacin III in deuterated dimethylsulfoxide.
Figure 12:
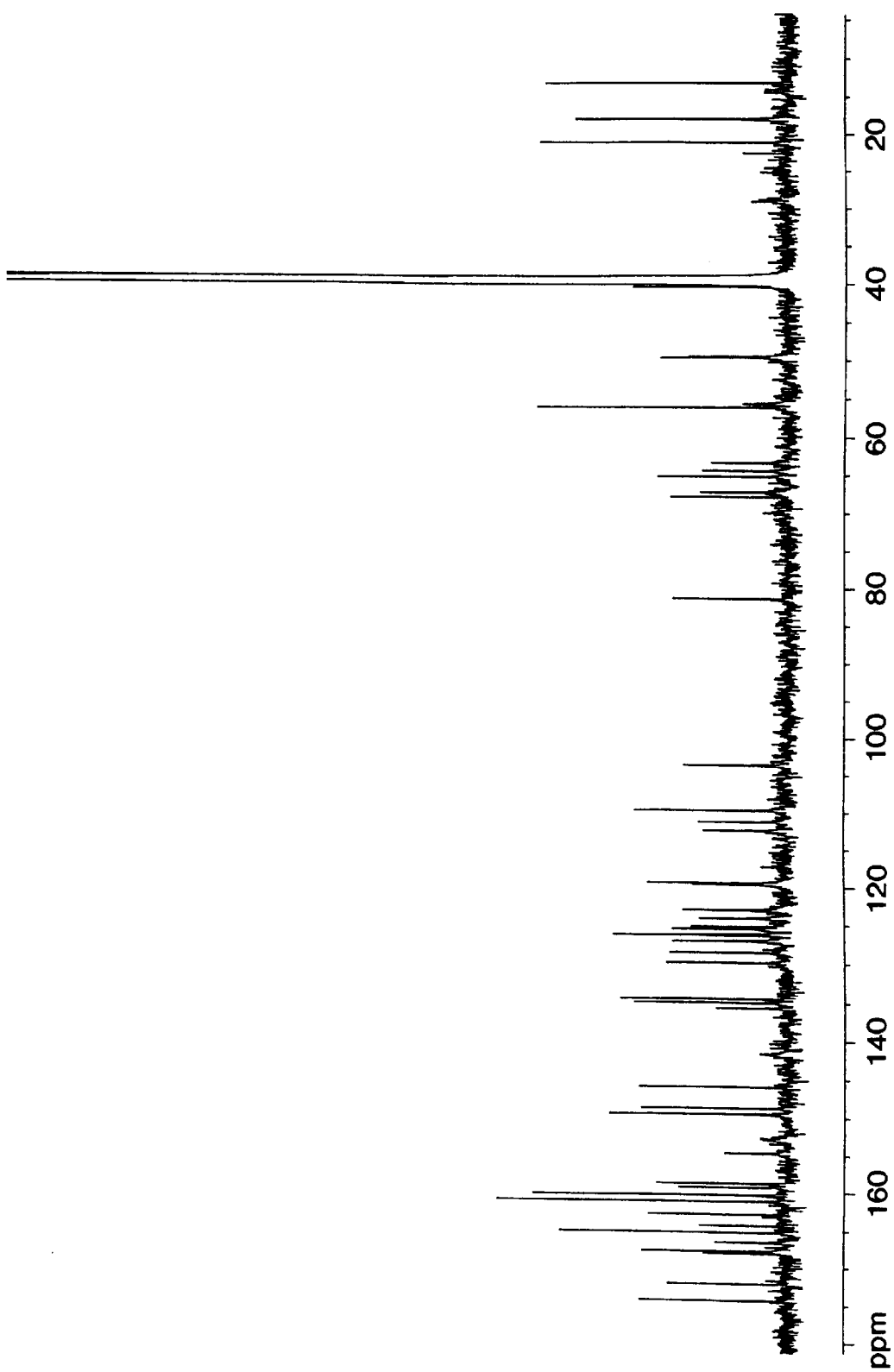
FIG. 12 shows the $^{13}$C-NMR (125 MHz) spectrum of nocathiacin III in deuterated dimethylsulfoxide.

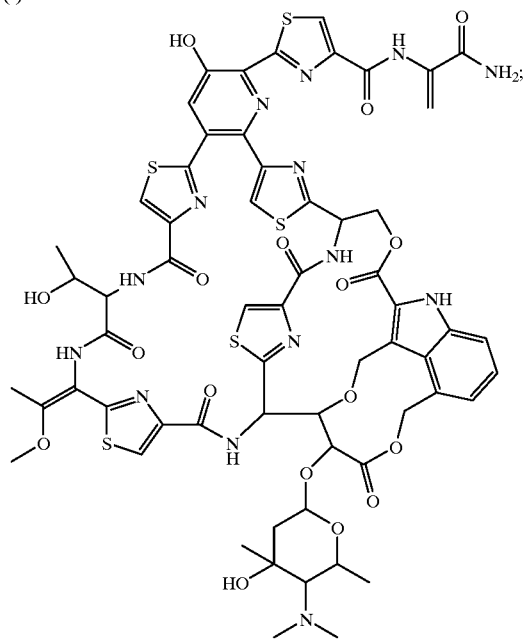

and wherein nocathiacin III has the following characteristics:

(a) appears as a buff colored amorphous solid;
(b) has a molecular weight of 1265 as determined by mass spectrometry;
(c) has the molecular formula $C_{52}H_{43}N_{13}O_{16}S_5$
(d) exhibits an ultraviolet absorption spectrum when dissolved in methanol substantially as shown in FIG. 9;
(e) exhibits an infrared absorption spectrum (KBr) substantially as shown in FIG. 10;
(f) when dissolved in deuterated dimethylsulfoxide exhibits a proton magnetic resonance spectrum substantially as shown in FIG. 11;
(g) when dissolved in deuterated dimethylsulfoxide exhibits a $^{13}C$ magnetic resonance spectrum substantially as shown in FIG. 12;
(h) exhibits a high performance liquid chromatography retention time of 19.3 minutes with a C18 reversed phase silica gel column using a 0.01M potassium phosphate buffer pH 3.5—acetonitrile gradient;
(i) and has the formula

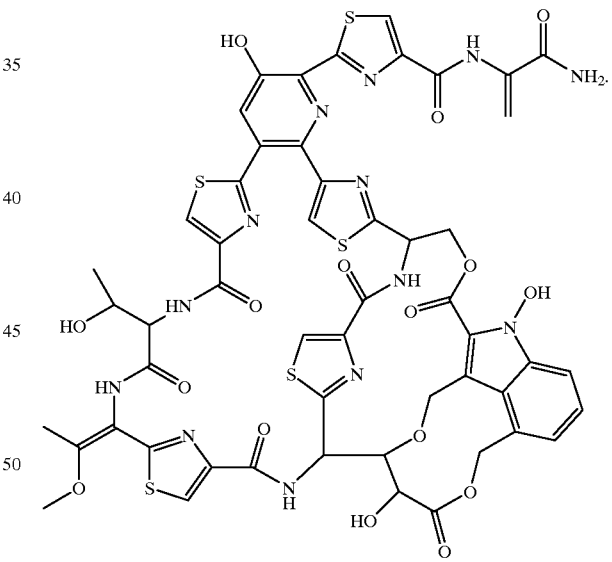

3. A compound of claim 1 which is nocathiacin I.
4. A compound of claim 1 which is nocathiacin II.
5. A compound of claim 1 which is nocathiacin III.
6. A pharmaceutical composition comprising a therapeutically effective amount of a compound as claimed in any of claims 1–5 and a suitable carrier or diluent.

7. A method for preventing or treating infection of a mammal by a bacterium, comprising the step of administering a therapeutically effective amount of a compound as claimed in any of claims 1–5 to said mammal in need thereof.

* * * * *